(12) United States Patent
Kemp

(10) Patent No.: US 6,840,244 B2
(45) Date of Patent: Jan. 11, 2005

(54) CONDOM WITH AN ERECTOGENIC COMPOSITION

(75) Inventor: Colin Anthony Kemp, Hampshire (GB)

(73) Assignee: Futura Medical Developments Limited, Surrey (GB)

( * ) Notice: Subject to any disclaimer, the term of this patent is extended or adjusted under 35 U.S.C. 154(b) by 0 days.

(21) Appl. No.: 10/473,120

(22) PCT Filed: Mar. 28, 2002

(86) PCT No.: PCT/GB02/01486

§ 371 (c)(1),
(2), (4) Date: Sep. 29, 2003

(87) PCT Pub. No.: WO02/078580

PCT Pub. Date: Oct. 10, 2002

(65) Prior Publication Data

US 2004/0103902 A1 Jun. 3, 2004

(30) Foreign Application Priority Data

Mar. 30, 2001 (GB) .............................. 0108027
May 18, 2001 (GB) .............................. 0112242
Jul. 23, 2001 (GB) .............................. 0117888
Oct. 23, 2001 (GB) .............................. 0125452

(51) Int. Cl.$^7$ ................................. A61F 6/04
(52) U.S. Cl. ................. 128/844; 128/898; 128/918; 604/347
(58) Field of Search ................. 128/844, 898, 128/917, 918, 842; 604/347, 349, 350, 351, 352, 353

(56) References Cited

U.S. PATENT DOCUMENTS

| 3,363,624 | A | | 1/1968 | Fishman | |
|---|---|---|---|---|---|
| 4,829,991 | A | | 5/1989 | Boeck | |
| 6,007,836 | A | | 12/1999 | Denzer | |
| 6,182,661 | B1 | * | 2/2001 | Solanki et al. | 128/844 |
| 6,223,747 | B1 | * | 5/2001 | Rudge et al. | 128/844 |
| 6,250,303 | B1 | * | 6/2001 | Delaney | 128/844 |
| 6,321,751 | B1 | * | 11/2001 | Strauss et al. | 128/844 |
| 6,453,903 | B1 | * | 9/2002 | Thomas, III | 128/844 |
| 6,523,540 | B1 | * | 2/2003 | Harrison | 128/844 |
| 6,651,667 | B2 | * | 11/2003 | Osterberg | 128/844 |
| 6,651,668 | B1 | * | 11/2003 | Praml | 128/844 |
| 6,718,983 | B1 | * | 4/2004 | Suzuki | 128/844 |
| 6,732,736 | B2 | * | 5/2004 | Sanchez | 128/844 |

FOREIGN PATENT DOCUMENTS

EP 0 934 744 A 8/1999

* cited by examiner

Primary Examiner—Fadi H. Dahbour
(74) Attorney, Agent, or Firm—Miles & Stockbridge P.C.; Dennis P. Clarke

(57) ABSTRACT

A condom has an erectogenic compound immobilised on the interior surface and substantially at the head end thereof. The compound may be applied as a component of a composition comprising the erectogenic compound dispersed or dissolved in a gel carrier comprising a liquid medium including a thickening agent. The condom may include a lubricant which may be immiscible with the erectogenic compound or composition. Use of the condom sustains e penile erection following spontaneous initiation thereof, to prevent slippage of the condom off the penis while intercourse takes place.

13 Claims, No Drawings

CONDOM WITH AN ERECTOGENIC COMPOSITION

This invention relates to condoms which have applied to their inner surfaces an erectogenic formulation for sustaining an erection of the penis, where the user may be incapable of sustaining a full erection while intercourse takes place. The loss of the ability to sustain a full erection, which may be age-related or due to an organic or psychological condition, or may occur naturally in an otherwise healthy adult, not only reduces sexual satisfaction but also increases the risk of condom failure due to slippage off the penis.

BACKGROUND OF THE INVENTION

Condoms including erectogenic formulations are generally already known for treatment of impotence, that is, the failure to achieve an erection, resulting in an inability to have intercourse at all. For example, U.S. Pat. No. 4,829,991 describes a condom in which the interior surface is coated with a erectogenic except at the open and closed end portions. The erectogenic may be a transdermal nitroglycerine coating the surface tension of which, under friction forces on initially fitting the condom to the penis, breaks down so that the coating makes contact with the skin of part of the shaft of the penis, thus resulting in the gradual development of an erection which enables fitting of the condom to be completed, whereafter optimal contact between the penis and the coating is achieved to enable intercourse to take place. U.S. Pat. No. 5,333,621 describes a condom the interior surface of which has a coating of a lubricant and vehicle containing a erectogenic, or in which the erectogenic is in the form of a transdermal patch applied to the wall of the condom by an adhesive which has a lower coefficient of adhesion to the condom wall than an adhesive on the other side of the patch has to the skin of the penis in use, provision being made for making the stronger adhesive pressure-sensitive whereby it can be activated by manual pressure applied by the user. U.S. Pat. No. 6,080,100 describes a condom or other support material having applied over substantially its entire inner surface a vasodilator-containing film including an adhesive carrier, optionally with a reservoir for further vasodilator-containing material at the head of the condom and sealed with an internal user-breakable membrane.

The prior proposals suffer from various disadvantages. For example, since condoms are generally sold in sealed packages in a rolled-up form ready to be applied to and unrolled along the shaft of the erect penis, there has been no allowance made for the desirability of avoiding transfer of the vasodilator composition from the inner to the outer wall of the condom during pre-use storage, to avoid the genitalia of the sexual partner of the user being exposed to the composition. Another disadvantage is that it is difficult to apply a condom to a penis which is not fully erect and it follows that a vasodilator composition applied to the penile shaft-contacting part of a condom wall will be largely ineffective in stimulating an erection.

OBJECTS OF THE INVENTION

It is an object of the present invention to provide an erectogenic composition which can be applied to the closed or head end of a condom and which remains substantially localised therein during storage and use and which is effective in sustaining an erection while intercourse takes place to reduce the risk of the condom failing as a barrier by slippage off a partially-erect penis.

According to one aspect of the invention, there is provided a condom having an erectogenic compound immobilised on the interior surface of the condom and substantially at the head end thereof.

In one embodiment, the erectogenic compound is applied to the condom as a composition comprising a solution or suspension in a solvent carrier, optionally with an adhesion or film-forming agent, the solvent subsequently being removed by evaporation to leave the erectogenic compound immobilised, preferably in finely-divided form or as a film layer, on the surface at the head end region of the condom.

In another embodiment, the erectogenic compound is applied to the interior head end region of a condom as a component of a composition comprising the erectogenic compound dispersed or dissolved in a gel carrier comprising a liquid medium including a thickening agent.

According to another aspect of the invention, there is provided an erectogenic composition for application to the interior head end region of a condom, the composition comprising an erectogenic compound dispersed or dissolved in a gel carrier comprising a liquid medium including a thickening agent.

In a further aspect, the invention provides the use of an erectogenic compound for application in immobilised relationship to the interior surface of a condom substantially at the head end thereof for sustaining a penile erection following spontaneous initiation thereof, to prevent slippage of the condom while intercourse takes place.

In yet a further aspect, the invention provides the use of an erectogenic compound in the preparation of a composition for application to the interior surface of a condom in immobilised relationship and substantially at the head end thereof, to sustain a penile erection following spontaneous initiation thereof.

The invention also provides a method of inhibiting the slippage of a condom from a penis during use of the condom, the method comprising applying to the interior surface of the condom at the head end region thereof an immobilised erectogenic compound which, during use of the condom, is transdermally absorbed by the penis to sustain the erection initiated spontaneously to maintain condom-retaining contact between the shaft of the penis and the condom.

DETAILED DESCRIPTION OF THE INVENTION

In this specification, references to the head end of the condom are intended to mean that portion at the closed end which, irrespective of the presence or absence of a sac, is in contact in use with the glans of the penis. Immobilisation of the erectogenic compound in this region prevents migration thereof during storage and use, whereby the erectogenic compound is prevented from reaching the outer surface of the condom and thus from contact with the sexual partner of the user.

References to the spontaneous initiation of an erection are intended mean to the initiation of an erection by virtue of natural stimuli including those associated with visual, aural or touch receptors.

Erectogenic compounds that can be incorporated into the condom include vasodilators or related compounds, including the nitrates, long and short acting alpha-adrenoceptor blockers, ergot alkaloids, anti-hypertenives and the prostaglandins. Phosphodiesterase inhibitors, particularly type III and IV and most particularly type V can also be used, either alone or in combination with vasodilators and related compounds.

Useful nitrates and similarly acting compounds include nitro-glycerine, isosorbide dinitrate, erythrityl tetranitrate, amyl nitrate, sodium nitroprusside, molsidomine, linsidomine chlorydrate ("SIN-1"), S-nitroso-N-acetyl-d,1-penicillamine ("SNAP"), S-nitroso-N-cysteine, S-nitroso-N-glutathione ("SNO-GLU") and diazenium diolates ("NONOates"). A particularly useful nitrate is nitro-glycerine.

Natural prostaglandins that can be used include $PGE_0$, $PGE_1$, $PGA_1$, $PGB_1$, $PGF_1$alpha, 19-hydroxy-$PGA_1$, 19-hydroxy-$PGB_1$, PGE2, $PGA_2$, $PGB_2$, 19-hydroxy-$PGA_2$, 19-hydroxy-$PGB_2$, $PGE_3$, $PGF_3$alpha. Semi synthetic and synthetic prostaglandins such as carboprost tromethamine, dinoprost tromethamine, dinoprostone, lipoprost, gemeprost, metenoprost, sulprostone and tiaprost can also be used. A particularly useful prostaglandin is prostaglandin $E_1$ ($PGE_1$) or its synthetic version, alprostadil. Esters of the prostaglandins, such as the methyl and ethyl esters, can also be used.

Suitable alpha-adrenoceptor blockers include phenoxybenzamine, dibenamine, doxazosin, terazosin, phentolamine, tolazoline, prazosin, trimazosin, alfuzosin, tamsulosin and indoramin.

Ergot alkaloids include ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride. A particularly effective alkaloid is yohimbine hydrochloride.

Non-specific phosphodiesterase inhibitors that can be incorporated into the condom include theophylline, IBMX, pentoxifylline and papaverine, and direct vasodilators such as hydralazine. Papaverine is particularly useful either alone or in combination with phentolamine.

Examples of type III phosphodiesterase inhibitors that may be used include bipyridines such as milrinone and amirinone, imidazolones such as piroximone and enoximone, dihydropyridazinones such as imazodan, 5-methyl-imazodan, indolidan and ICI1118233, quinolinone compounds such as cilostamide, cilostazol and vesnarinone, and other molecules such as bemoradan, anergrelide, siguazodan, trequinsin, pimobendan, SKF-94120, SKF-95654, lixazinone and isomazole.

Examples of suitable type IV phosphodiesterase inhibitors include rolipram and rolipram derivatives such as RO20-1724, nitraquazone and nitraquazone derivatives such as CP-77059 and RS-25344-00, xanthine derivatives such as denbufylline and ICI63197, and other compounds such as EMD54622, LAS-31025 and etazolate.

Examples of type V phospodiesterase inhibitors include zaprinast, MY5445, dipyridamole, vardenafil, and sildenafil. Other suitable type V phosphodiesterase inhibitors are disclosed in PCT Publication Nos. WO 94/28902 and WO 96/16644. A particularly useful type V phosphodiesterase inhibitor is sildenafil. Still other type V phosphodiesterase inhibitors useful in conjunction with the present invention include: IC-351 (ICOS); 4-bromo-5-(pyridylmethylamino)-6-[3-(4-chlorophenyl)propoxy]-3(2H)pyridazinone; 1-[4-[(1,3-benzodioxol-5-ylmethyl)amiono]-6-chloro-2-quinazolinyl]4-piperidine-carboxylic acid, monosodium salt; (+)-cis-5,6a,7,9,9a-hexahydro-2-[4-(trifluoromethyl)-phenylmethyl-5-methyl-cyclopent-4,5]imidazo(2,1-b]purin-4(3H)one, furazlocillin; cis-2-hexyl-5-methyl-3,4,5,6a,7,8, 9,9a-octahydrocyclopent[4,5]imidazo[2,1-b]purin-4-one; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; 1-methyl-5-(5-morpholinoacetyl-2-n-propoxyphenyl)-3-n-propyl-1,6,-dihydro-7H-pyrazolo(4,3-d)pyrimidin-7-one; 1-[4-[1,3-benzodioxol-5-ylmethyl)amino]-6-chloro-2-quinazolinyl]4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Scherin Plough); GF-196960 (Glaxo Wellcome); and Sch-51866.

Other compounds that can be used include nimodipine, pinacidil, cyclandelate, isoxsuprine, chloromazine, haloperidol, Rec15/2739 and trazodone, as well as antihyertensive agents including diazoxide, hydralazine and minoxidil.

The above active agents, either alone or in combination, can be used together with skin penetration enhancers such as azone (1-n-dodecylcyclazacycloheptan-2-one). Other permeation enhancers include dimethylsulfoxide (DMSO), dimethyl formamide(DMF), N,N-dimethylacetamide (DMA), decylmethylsulfoxide ($C_{10}$MSO), polyethylene glycol monolaurate (PEGML), glycerol monolaurate, lecithin and 1-substituted azacycloheptan-2-one.

The gel carrier for the active ingredient should have sufficient viscosity to ensure that the composition remains localised at or close to the head end of the condom during storage and the liquid medium is preferably viscous at ordinary temperatures.

In most cases, the condom also includes a lubricant. Preferably, the lubricant is immiscible with the erectogenic compound or the composition containing the erectogenic component. The lubricant can be water based or can be a silicone based oil with a viscosity of approximately 200 cP, in order to discourage migration of the composition by gradual mixing with the lubricant and spreading by capillary action between adjacent rolls of the condom which, if allowed to happen, would result in deposition of the composition on both the inner and outer surfaces of the condom.

The rheological properties of the gel are preferably such that the viscosity becomes lowered in use, preferably by a thixotropic effect whereby the gel structure breaks down under shear forces on being initially contacted by the penis to cause the active compound to be uniformly distributed over the head or glans of the penis for rapid absorption.

The thickening or gelling agent may be inorganic or organic or a mixture thereof. Inorganic thickening agents may include montmorrillonite-containing clays such as bentonite and hectorite, silica gel and the like and organic thickening agents may comprise waxes or polymers soluble or dispersible in the liquid medium. When the lubricant is water based, the medium preferably comprises a vegetable oil, for example castor oil. When the lubricant is oil based, the medium preferably comprises a polyhydroxy compound such as propylene glycol especially where the erectogenic compound comprises nitroglycerine, since propylene glycol is miscible with nitroglycerine and is sufficiently high-boiling or non-volatile to maintain the composition physically stable on storage and use. However, other suitable polyhydroxy compounds include glycerol and low molecular weight polymers of, for example, ethylene glycol. Water-miscibility is preferred especially so that residues may readily be washed off the penis and it is also preferred for the composition to be inert to semen. A class of organic thickening agent suitable for use in the present invention comprises water-miscible polymers of a methacrylic ester. Other suitable thickening agents include cellulose derivatives, for example, methyl cellulose, carboxymethyl cellulose, hydroxyethyl cellulose and hydroxypropyl cellulose; polyvinylalcohol; polyvinylpyrolliodone and acrylic acid derviatives such as polyacrylic acid and polymethacrylic acid, optionally partially cross-linked.

Examples of particular thickening agents which may be used especially with castor oil as the liquid medium include Bentone gel CAO-V, a commercially-available hectorite; Jojoba Glaze LV or Jojoba Glaze HV, mixtures of jojoba oil and Versagel, itself a mixture of ethylene/propylene/styrene copolymer and butylene/ethylene/styrene copolymer; ceresine wax; carnaube wax, for example Carauba Wax; candelilla wax, for example Candilla Wax; and Unitwix, a mixture of tristearin and a $C_{18-36}$ carboxylic acid glycol ester.

To form a composition according to the invention, the erectogenic compound and optionally skin penetration enhancer may be dissolved in the medium, which should be inert to the material of the condom, and admixed with the thickening agent optionally with addition of water (or oil solvent, as appropriate) to achieve the intended concentration of active ingredient and rheological properties.

A predetermined or metered amount of the composition is then added, for example by injection, to the closed end of a rolled condom before the condom is packaged and sealed. The lubricant is added at the same stage in conventional manner but, while the lubricant will migrate to coat substantially the entire inner and outer surfaces of the condom, the erectogenic compound-containing formulation will remain in place at the closed end of the condom.

Embodiments of the invention will now be described by way of example.

EXAMPLE 1

To a gel composition available commercially as "Lubragel CG" and containing glyceryl polymethacrylate (67%), water (30%) and monopropylene glycol (1%), together with methyl and propyl paraben as stabilizers, was added a solution of nitroglycerine in propylene glycol to give a concentration of nitroglycerine of between 0.4 and 4.0% by weight and a water concentration of 15 to 25%, say 18% for a gel containing 2% nitroglycerine. 250 mg of the composition is then applied to the closed end of a condom and packaged. The condom may be made from a latex material or a polyurethane film material. The gel composition is suitable for use with a condom having a silicone fluid lubricant.

EXAMPLE 2

A gel was manufactured from castor oil BP and a gelling agent commercially available as "Miglyol Gel B" containing caprylic/capric triglyceride (greater than 50%), stearalkonium hectorite (10–25%) and propylene carbonate (1-5%) to which was added nitroglycerine absorbed on lactose (10%) to give a concentration in the range 0.1 to 4% by weight in the final gel formulation, that is, a 40% concentration in lactose to give a 4% overall concentration.

EXAMPLE 3

A gel was manufactured from castor oil BP and "Bentone" gel CAO-V as gelling agent containing castor oil (approximately 87%), stearalkonium hectorite (approximately 10%), propylene carbonate (approximately 3%) and a commercially available antioxidant, namely Tenox (approximately 0.1%) containing propylenene glycol approximately 70%, butylated hydroxy anisole approximately 20%, propyl gallate approximately 6% and citric acid approximately 4%, to which was added nitroglycerine absorbed on lactose (10%) to give a concentration of 0.1 to 4%, say 40% on lactose for a gel containing 4% nitroglycerine.

EXAMPLE 4

A gel was manufactured from castor oil BP and a commercially available fumed silica (Neocil Ctl1) to which was added nitroglycerie absorbed on to lactose (10%) to give a concentration of 0.1 to 4% say 40% on lactose for a gel containing 4% nitroglycerine.

The gel formulations of Example 2 to 4 may be applied to the head end of a condom as described with references to Example 1. The formulations are suitable for use with condoms having water-based lubricants.

In use, the condom is removed from its packaging and the closed end with the erectogenic composition coated thereon is applied to the tip of the penis as an initial step before unrolling the condom over the penile shaft. It is assumed that the penis is already fully erect but, should the penis not have achieved such a state, rendering both condom application and intercourse difficult to achieve, the erectogenic composition will be rapidly absorbed through the head of the penis which will thus more easily attain an erect state whereby both complete application of the condom and subsequent intercourse can be achieved. The composition in use remains localized in the head region of the condom and does not become transmitted to the sexual partner. The maintenance of a full erection while intercourse takes place reduces the risk of condom failure which would otherwise have occurred due to slippage off the penis, should the quality of the erection have deteriorated.

What is claimed is:

1. A condom having an erectogenic compound or a composition containing an erectogenic compound localised on the interior surface and substantially at the head end thereof, said condom including a lubricant which is immiscible with said erectogenic compound or composition.

2. A condom according to claim 1, in which the erectogenic compound comprises a vasodilator.

3. A condom according to claim 2, in which the vasodilator is selected from nitrates, long and short acting alpha-adrenoceptor blockers, ergot alkaloids, anti-hypertenives and the prostaglandins.

4. A condom according to claim 1, in which the erectogenic compound comprises a phosphodiesterase inhibitor.

5. A condom according to claim 4, in which the phosphodiesterase inhibitor comprises papaverine optionally in combination with phentolamine.

6. A condom according to claim 1, in which the erectogenic composition includes a skin penetration enhancer.

7. A condom according to claim 1, in which the erectogenic composition comprises an erectogenic compound dispersed or dissolved in a gel carrier comprising a liquid medium including a thickening agent.

8. A condom according to claim 1, in which the thickening or gelling agent is inorganic or organic or a mixture thereof, inorganic thickening agents comprising montmorrillonite-containing clays such as bentonite and hectorite or silica gel and organic thickening agents comprising polymers soluble or dispersible in the liquid medium.

9. A condom according to claim 1, in which the erectogenic compound is applied as a solution or suspension in a solvent carrier, optionally with an adhesion or film-forming agent, the solvent subsequently being removed by evaporation to leave the erectogenic compound localised, preferably in finely-divided form or as a film layer, on the surface at the head end region of the condom.

10. An erectogenic composition for application substantially to the interior head end region of a condom including a lubricant, the composition comprising an erectogenic compound dispersed or dissolved in a gel carrier comprising a liquid medium including a thickening agent, the lubricant and composition being immiscible.

11. The use of an erectogenic compound or composition for sustaining a penile erection following spontaneous initiation thereof, to prevent slippage of the condom while intercourse takes place, by application of the compound or composition in localised relationship to the interior surface of a condom substantially at the head end thereof, the condom including a lubricant and the compound or composition being immiscible with said lubricant.

12. The use of an erectogenic compound in the preparation of a composition for application to the interior surface of a condom in localised relationship and substantially at the head end thereof, to sustain a penile erection following spontaneous initiation thereof, the condom including a lubricant and the composition being immiscible with said lubricant.

13. A method of inhibiting the slippage of a condom from a penis during use of the condom, the method comprising applying to the interior surface of the condom and localised substantially at the head end region thereof an erectogenic compound or composition which, during use of the condom, is transdermally absorbed by the penis to sustain the erection initiated spontaneously to maintain condom-retaining contact between the shaft of the penis and the condom, the condom including a lubricant and the compound or composition being immiscible with said lubricant.

* * * * *

Disclaimer

6,840,244 — Colin Anthony Kemp, Hampshire (GB). CONDOM WITH AN ERECTOGENIC COMPOSITION. Patent dated January 11, 2005. Disclaimer filed May 5, 2006, by the assignee, Futura Medical Development Limited.

Hereby enters this disclaimer to claim 10 of said patent.

*(Official Gazette, May 27, 2008)*